US00PP33752P2

(12) United States Plant Patent
Egger

(10) Patent No.: US PP33,752 P2
(45) Date of Patent: Dec. 14, 2021

(54) ***SEDUM* PLANT NAMED 'CONGA LINE'**

(50) Latin Name: *Sedum (Hylotelephium) telephium*
Varietal Denomination: Conga Line

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/338,506

(22) Filed: Jun. 3, 2021

(51) Int. Cl.
*A01H 5/02* (2018.01)
*A01H 6/80* (2018.01)

(52) U.S. Cl.
USPC ..... Plt./479

(58) Field of Classification Search
USPC ..... Plt./479
See application file for complete search history.

*Primary Examiner* — Susan McCormick Ewoldt
(74) *Attorney, Agent, or Firm* — Klarquist Sparkman, LLP

(57) ABSTRACT

A new and distinct hybrid of *Sedum* plant substantially as shown and described characterized by glossy, yellow-green to greyed-purple leaves with red serrated leaf margins, showy foliage appearing in even ranks around the stem, strongly upright reddish purple stems, a medium, clumping habit, and excellent vigor.

2 Drawing Sheets

Botanical denomination: *Sedum* (*Hylotelephium*) *telephium.*

Variety designation: 'Conga Line'.

BACKGROUND OF THE INVENTION

The present invention relates to a new and distinct cultivar of *Sedum* (*Hylotelephium*) and given the cultivar name of 'Conga Line'. *Sedum* is in the family Crassulaceae. *Sedum* 'Conga Line' originated from a planned cross for compact multicrowned *Sedum* using *Sedum* 436-1, as the seed parent, and *Sedum* 420-8, as the pollen parent. Both parents are unnamed proprietary, unpatented *Sedum telephium* seedlings.

Compared to *Sedum telephium* 436-1, the seed parent, the new cultivar has glossy, yellow-green to greyed-purple leaves with red leaf margins and reddish purple stems rather than green leaves with pink stems.

Compared to *Sedum telephium* 420-8, the pollen parent, the new cultivar has glossy, yellow-green to greyed-purple leaves with red leaf margins and reddish purple stems with multiple crowns rather than dark red leaves and few crowns.

Compared to *Sedum* 'Rosetta', U.S. Plant Pat. No. 26,190, the new cultivar has glossy, yellow-green to greyed-purple leaves with red leaf margins and reddish purple stems rather than blue-green leaves and green stems.

This new and unique *Sedum* is distinguished by:

1. glossy, yellow-green to greyed-purple leaves with serrated leaf margins,
2. showy foliage appearing in even ranks around the stem,
3. strongly upright reddish purple stems,
4. a medium, clumping habit, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
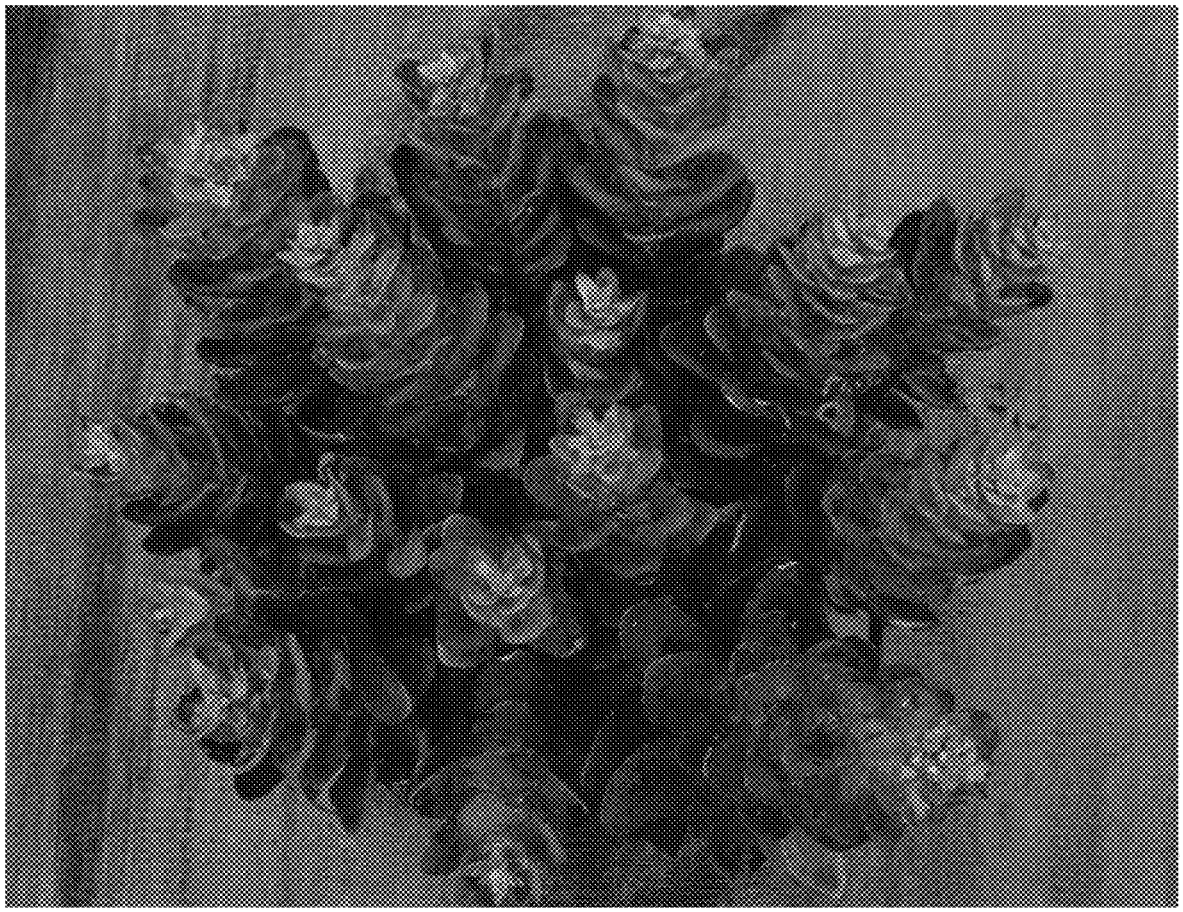
FIG. 1 shows a one and a half-year-old *Sedum* 'Conga Line' in bud growing in full sun in the trial bed outside in late July in Canby, Oreg.
Figure 2:
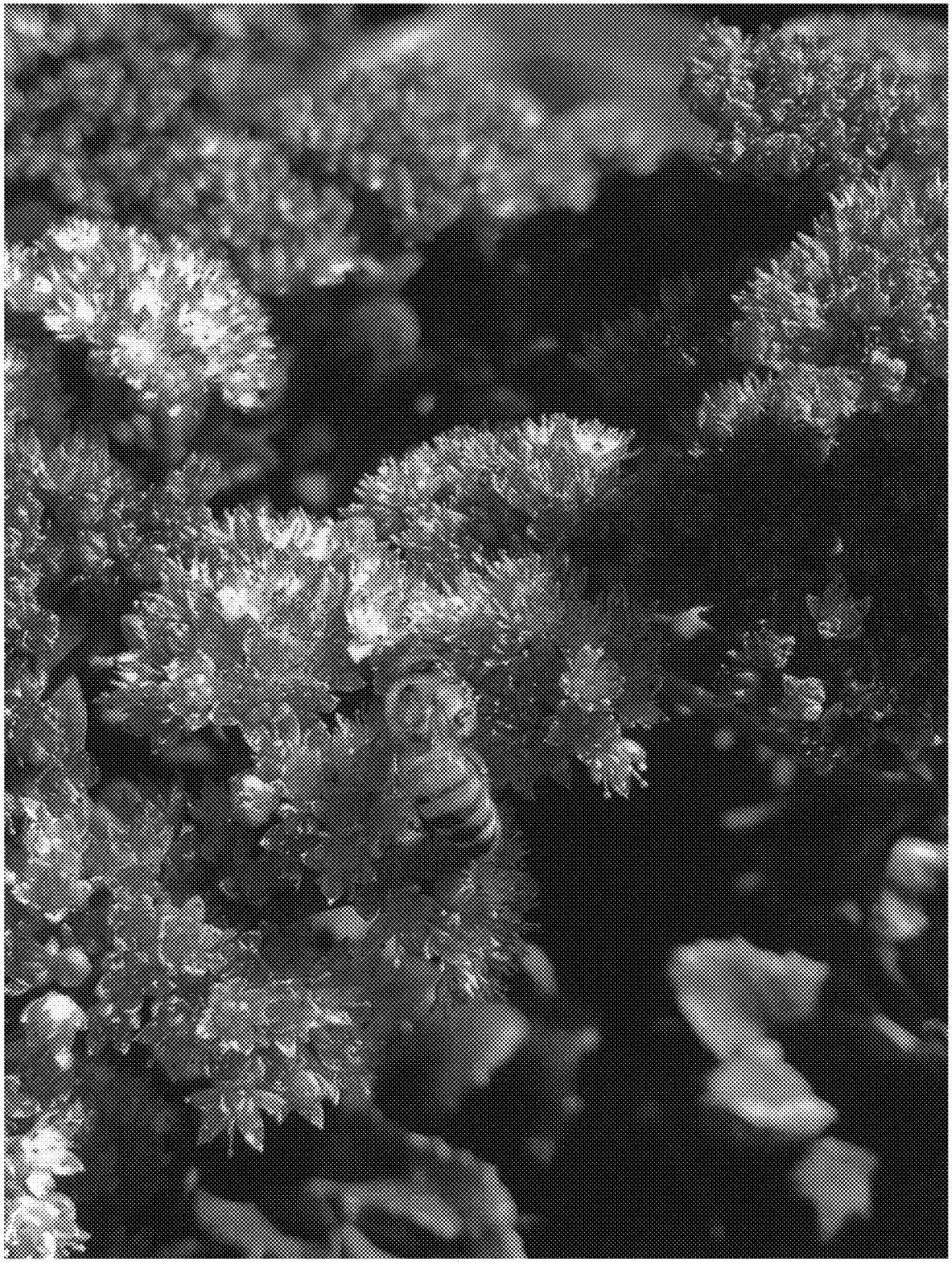
FIG. 2 shows a close-up of the inflorescence.

The following is a detailed description of the new *Sedum* hybrid based on observations of three-year-old specimens grown in the trial bed in full sun under typical outdoor conditions in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The Royal Horticultural Society Colour Chart, 5$^{th}$ edition, 2007.

Plant:

*Type.*—Herbaceous perennial.
*Hardiness.*—USDA Zone 4 to 9.
*Size.*—54 cm tall from the ground to the top of the inflorescence and 57 cm wide.
*Habit.*—Erect, clumping.
*Vigor.*—Excellent.

Stem: unbranched.

*Number.*—About 30.
*Size.*—Grows to 41 cm long and 8 mm wide.
*Internode length.*—7 mm to 12 mm.
*Surface.*—Glabrous, glossy.
*Color.*—Red Purple 61A.

Leaf:

*Type.*—Simple.

*Arrangement.*—Alternate.

*Shape.*—Ovate.

*Apex.*—Acute.

*Base.*—Truncate to slightly cordate.

*Venation.*—Pinnate.

*Margins.*—Irregularly serrate.

*Blade size.*—Grows to 6 cm long and 2.5 cm wide.

*Surface.*—Glabrous on both sides.

*Texture.*—Succulent.

*Petiole.*—None, leaves sessile.

*Leaf color.*—Summer topside Yellow Green 147A, blending to Purple N79A at margin, including the vein, bottom side Green 147B heavily tinted Greyed Purple 187A, vein Greyed Purple 187B; spring topside Yellow-Green 147B, blending to 61B at margin, bottom side Green 189A lightly tinted Greyed Purple N187B, vein Greyed Red 181A.

Inflorescence:

*Type.*—Terminal, corymbose, umbel-like.

*Number of flowers.*—About 850 per stem.

*Peduncle.*—None.

*Rachis.*—About 5 cm long and 5 mm wide, Red Purple 61A, succulent, glabrous.

*Pedicels.*—Grows to 3 mm to 4 mm long and 1 mm wide, glaucous, Greyed Yellow 161C.

*Size.*—Grows to 6 cm to 7 cm deep and 2.75 cm wide.

*Bloom period.*—August through September in Canby, Oreg.

Flower bud:

*Size.*—2.5 mm wide, 3.5 mm deep.

*Description.*—Conical.

*Color.*—Greyed Purple 184C on top half blending to 186B.

Flower:

*Type.*—Complete, actinomorphic.

*Shape.*—Stellate.

*Size.*—6 mm deep and 8 mm wide.

*Color.*—Red Purple 62D.

*Corolla description.*—4 mm deep and 5.5 mm wide, 5 petals, each lanceolate, cupped, 5 mm long and 1.5 mm wide, margins entire, tip acuminate, base rounded, both sides glabrous and Orange-White 159D on top half and darkening to Greyed Purple 186C on bottom.

*Calyx description.*—1.5 mm deep and 2.5 mm wide, campanulate, 5 lobes, divided to the base, margins entire, tip acuminate, glabrous, Brown 200A on both sides.

*Stamen description.*—8 in number, 3 mm long, filaments 3 mm long, Red Purple 64D, anthers 0.5 mm deep, shriveled, Greyed Purple 185D, very little pollen White NN155A.

*Pistil description.*—5 separate prominent carpels, each 3 mm deep and 1.5 mm wide, Greyed Purple 185C on top half to Greyed Purple 186D on bottom half with stigma Greyed Purple 187B.

*Fragrance.*—None.

*Lastingness.*—Each stem lasts up to a month.

Fruit:

*Type.*—Ventrally dehiscent follicle, erect, attenuate.

*Fertility.*—None.

*Color.*—Brown 200A.

Seed: None seen.

Disease and Pest Resistance or Tolerance: Pest and disease resistance are typical for this type of *Sedum*.

I claim:

1. A new and distinct *Sedum* plant as herein illustrated and described.

* * * * *